United States Patent
Collins et al.

(10) Patent No.: US 10,143,664 B2
(45) Date of Patent: *Dec. 4, 2018

(54) METHOD FOR IMPROVING FEED EFFICIENCY IN RUMINANTS

(71) Applicant: Rivalea (Australia) Pty Ltd, Corowa (AU)

(72) Inventors: Cherie Louise Collins, Corowa (AU); Brian Gerard Luxford, Wangaratta (AU)

(73) Assignee: RIVALEA (AUSTRALIA) PTY LTD, Corowa (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/128,771

(22) PCT Filed: Mar. 25, 2015

(86) PCT No.: PCT/AU2015/000172
§ 371 (c)(1),
(2) Date: Sep. 23, 2016

(87) PCT Pub. No.: WO2015/143483
PCT Pub. Date: Oct. 1, 2015

(65) Prior Publication Data
US 2017/0105949 A1    Apr. 20, 2017

(30) Foreign Application Priority Data
Mar. 26, 2014    (AU) .................................. 2014901085

(51) Int. Cl.
*A61K 31/137* (2006.01)
*A61K 31/522* (2006.01)
*A23K 50/10* (2016.01)
*A23K 20/111* (2016.01)
*A23K 20/137* (2016.01)

(52) U.S. Cl.
CPC .......... *A61K 31/137* (2013.01); *A23K 20/111* (2016.05); *A23K 20/137* (2016.05); *A23K 50/10* (2016.05); *A61K 31/522* (2013.01)

(58) Field of Classification Search
None
See application file for complete search history.

(56) References Cited

U.S. PATENT DOCUMENTS

| | | | |
|---|---|---|---|
| 3,852,451 A | 12/1974 | Cunningham | |
| 4,690,951 A | 9/1987 | Anderson et al. | |
| 5,422,352 A * | 6/1995 | Astrup ................ | A61K 31/475 514/263.31 |
| 2009/0143480 A1 | 6/2009 | Aberg et al. | |

FOREIGN PATENT DOCUMENTS

WO    2014056029 A1    4/2014

OTHER PUBLICATIONS

Quinn et al. in Journal of Animal Science 86(4), 902-908 (2008) (Year: 2008).*
Collins et al., "Maintaining the Response to Ractopamine Through Intermittent Feeding. 2H-102 Report prepared for the Co-operative Research Centre for an Internationally Competitive Pork Industry," Pork CRC, Jul. 2010, 1-13.
Li et al., "The Effect of Caffeine on Mammary Gland Development and Milk Yield in Primiparous Sows," J. Anim. Sci., 1995, 73:534-540.
Oksbjerg et al., "Separate and Combined Effects of Ephedrine and Caffeine on Protein and Lipid Deposition in Finishing Pigs," Animal Science, 1995, 60:299-305.
International Preliminary Report on Patentability, International Application No. PCT/AU2015/000172, dated May 19, 2015, 4 pages.

* cited by examiner

*Primary Examiner* — Dennis Heyer
(74) *Attorney, Agent, or Firm* — Morgan, Lewis & Bockius, LLP

(57) ABSTRACT

The technology relates to a method of increasing ractopamine response in a ruminant by feeding a ruminant an animal feed containing a synergistic combination of ractopamine and caffeine to extend the response to ractopamine in the ruminant.

21 Claims, No Drawings

METHOD FOR IMPROVING FEED EFFICIENCY IN RUMINANTS

TECHNICAL FIELD

The present technology relates to increasing ractopamine response in ruminants which can improve feed efficiency.

BACKGROUND

Beta adrenergic agonists (β-agonists), or phenethanolamines, are registered around the world for use in targeted livestock species to improve lean tissue deposition and feed efficiency. Two β-agonists are approved for use in ruminant animals (specifically cattle) in targeted markets (United States, Mexico, Canada and South Africa). The first is Ractopamine hydrochloride (RAC, Optaflexx™, Elanco Animal Health, Greenfield, Ind.) registered to improve growth performance, feed efficiency and carcass characteristics, while the second Zilpaterol hydrochloride (Zilmax™, Merck Animal Health) is approved for use during the finisher period to increase live weight gain and improve feed efficiency of cattle. Although both compounds are β-agonists, the products act with differing affinity on β-receptors. Both products are cleared from the animal rapidly, reflected in the NIL or very short (12 hr) withhold restrictions across animal species and in a range of markets. In addition to the product registrations for use in cattle, several research papers have observed similar improvements in growth performance and feed efficiency with RAC or Zilpaterol supplementation in lambs at constant or step up inclusion rates between 10-30 ppm. The label recommendations for Optaflexx™ suggest a dose of 11-27 ppm for growth; feed efficiency and carcass leanness improvements in cattle. The majority of studies investigating the effects of RAC on lamb performance utilise concentrations around 20 ppm (20 g/t). Given Zilpaterol is not approved for use in Australia in any animal species, the following investigation focused on ractopamine.

One of the issues with the use of β-agonists for improving growth performance and feed efficiency is that the response diminishes over time due to the down regulation of β-receptors. It would be advantageous if the response to β-agonists for improving growth performance and feed efficiency could be prolonged.

The present inventors have developed a method for prolonging the feed efficiency benefits of ractopamine and improving body composition by increasing lean tissue and reducing adipose tissue deposition in ruminants.

SUMMARY

The present technology is based on the surprising and unexpected finding that an animal feed containing a synergistic combination of ractopamine and caffeine can prolong and extend the response in a ruminant to ractopamine in an animal feed. It is well established that ractopamine has a beneficial effect for improving feed efficiency and weight gain in a range of animal species, with the maximal response observed within the first 3 weeks of feeding and declining thereafter. The present inventors have found that the use of caffeine in combination with ractopamine in an animal feed can extend the ractopamine response past 3 weeks to improve feed efficiency for lean tissue deposition in a ruminant.

In a first aspect, there is provided a method for increasing ractopamine response in a ruminant, the method comprising feeding a ruminant an animal feed containing a synergistic combination of ractopamine and caffeine to extend the response to ractopamine in the ruminant.

In an embodiment, the ruminant is selected from cattle, sheep, goat and deer. In one embodiment the ruminant is cattle.

In an embodiment, the ractopamine response is extended in the ruminant past about 21 days.

In an embodiment, the ractopamine response is improved feed efficiency for lean tissue deposition in the ruminant.

In an embodiment, the response to ractopamine in the ruminant is extended for at least 1 day or 2 days or 3 days or 4 days or 5 days or 6 days or 7 days or 8 days or 9 days or 10 days or 11 days or 12 days or 13 days or 14 days or 15 days or 16 days or 17 days or 18 days or 19 days or 20 days or 21 days or 22 days or 23 days or 24 days or 25 days or 26 days or 27 days or 28 days or 29 days or 30 days or 31 days or 32 days or 33 days or 34 days or 35 days or 36 days or 37 days or 38 days or 39 days or 40 days.

In an embodiment, the response to ractopamine in the ruminant is extended for at least about 7 days.

In an embodiment, the response to ractopamine in the ruminant is extended for at least about 14 days.

In an embodiment, the ruminant is fed an animal feed containing ractopamine and caffeine over a period of at least about 28 days.

In an embodiment, the ruminant is fed an animal feed containing ractopamine and caffeine for a period of about 21 to 35 days.

In an embodiment, the ruminant is fed an animal feed containing ractopamine and caffeine over a period of up to about 60 days.

In an embodiment, the ractopamine is ractopamine hydrochloride.

In an embodiment, the animal feed contains from about 1 mg/kg to 50 mg/kg (w/w) ractopamine and from about 0.02 g/kg to 5 g/kg (w/w) caffeine.

In an embodiment, the animal feed contains from about 5 mg/kg to 20 mg/kg (w/w) ractopamine and from about 0.1 g/kg to 1 g/kg (w/w) caffeine.

In an embodiment, the animal feed contains about 20 mg/kg ractopamine and about 0.5 g/kg caffeine.

In an embodiment, the animal feed is a typical ruminant finishing feed containing essential dietary requirements for a ruminant or as a top dress feed.

In an embodiment, the animal feed contains a range of energy and protein sources selected from wheat, barley, millmix, sorghum, corn, soybean meal, lupins, canola meal, molasses, and urea.

In an embodiment, the feed efficiency for lean tissue deposition of a ruminant is improved by about 1 to 50%.

In an embodiment, the feed efficiency for lean tissue deposition of a ruminant is up to about 50% improvement above feeding ractopamine alone over the same period.

In an embodiment, the animal feed may be supplemented with an animal feed supplement containing a synergistic combination of ractopamine and caffeine.

In an embodiment the animal feed supplement contains ractopamine hydrochloride and has a ratio of ractopamine to caffeine of from about 1:100 to 1:10.

In an embodiment, the ratio of ractopamine to caffeine is about 1:25.

In an embodiment, the supplement contains from about 1 to 50 g/kg ractopamine and from about 50 to 1000 g/kg caffeine for mixing with bulk complete animal feed to provide a desired final concentration of ractopamine and caffeine to the animal feed or for feeding to feed lot cattle or other ruminants as a top dress feed.

In an embodiment, the animal feed supplement contains at least about 10 g/kg ractopamine hydrochloride and at least about 250 g/kg caffeine.

In an embodiment, the animal feed supplement contains at least about 1% (w/w) ractopamine and at least about 50% (w/w) caffeine.

In a second aspect, there is provided a method to improve feed efficiency for lean tissue deposition in a ruminant, the method comprising feeding a ruminant an animal feed containing ractopamine for a first feeding period followed by feeding the ruminant an animal feed containing a synergistic combination of ractopamine and caffeine for a second feeding period to improve feed efficiency in the ruminant.

In an embodiment, the first feeding period is up to about 21 days and the second feeding period in up to about 40 days.

In an embodiment, the ruminant is fed an animal feed containing ractopamine over the first feeding period for at least 7 days or 8 days or 9 days or 10 days or 11 days or 12 days or 13 days or 14 days or 15 days or 16 days or 17 days or 18 days or 19 days or 20 days or 21 days.

In an embodiment, the ruminant is fed an animal feed containing ractopamine over the first feeding period for 14 to 21 days.

In an embodiment, the ruminant is fed an animal feed containing ractopamine and caffeine over the second feeding period for 7 days to 35 days.

In an embodiment, the ruminant is fed an animal feed containing ractopamine and caffeine over the second feeding period for at least 1 day or 2 days or 3 days or 4 days or 5 days or 6 days or 7 days or 8 days or 9 days or 10 days or 11 days or 12 days or 13 days or 14 days or 15 days or 16 days or 17 days or 18 days or 19 days or 20 days or 21 days or 22 days or 23 days or 24 days or 25 days or 26 days or 27 days or 28 days or 29 days or 30 days or 31 days or 32 days or 33 days or 34 days or 35 days or 36 days or 37 days or 38 days or 39 days or 40 days.

In an embodiment, the ruminant is fed an animal feed containing ractopamine and caffeine over the second feeding period for at least about 7 days.

In an embodiment, the ruminant is fed an animal feed containing ractopamine and caffeine over the second feeding period for at least about 14 days.

In an embodiment, the ruminant is fed an animal feed containing ractopamine and caffeine over the second feeding period for at least about 28 days.

In an embodiment, the ruminant is fed an animal feed containing ractopamine and caffeine over the second feeding period for about 21 to 35 days.

In an embodiment, the ruminant is fed an animal feed containing ractopamine for up to about 60 days.

In an embodiment, the ractopamine is ractopamine hydrochloride.

In an embodiment, during the first feeding period the animal feed contains from about 1 mg/kg to 50 mg/kg (w/w) ractopamine.

In an embodiment, the animal feed contains from about 5 mg/kg to 20 mg/kg (w/w) ractopamine.

In an embodiment, the animal feed contains about 20 mg/kg ractopamine.

In an embodiment, during second feeding period the animal feed contains from about 1 mg/kg to 50 mg/kg (w/w) ractopamine and from about 0.02 g/kg to 5 g/kg (w/w) caffeine.

In an embodiment, the animal feed contains from about 5 mg/kg to 20 mg/kg (w/w) ractopamine and from about 0.1 g/kg to 1 g/kg (w/w) caffeine.

In an embodiment, the animal feed contains about 20 mg/kg ractopamine and about 0.5 g/kg caffeine.

In an embodiment, the ruminant is fed ractopamine and caffeine over the second feeding period for at least 1 day or 2 days or 3 days or 4 days or 5 days or 6 days or 7 days or 8 days or 9 days or 10 days or 11 days or 12 days or 13 days or 14 days or 15 days or 16 days or 17 days or 18 days or 19 days or 20 days or 21 days or 22 days or 23 days or 24 days or 25 days or 26 days or 27 days or 28 days or 29 days or 30 days or 31 days or 32 days or 33 days or 34 days or 35 days or 36 days or 37 days or 38 days or 39 days or 40 days.

In an embodiment, the ruminant is fed ractopamine and caffeine for at least about 7 days.

In an embodiment, the ruminant is fed ractopamine and caffeine for at least about 14 days.

In an embodiment, the ruminant is fed ractopamine and caffeine for a period of about 21 to 35 days.

In an embodiment, the ruminant is fed ractopamine and caffeine over a period of up to about 60 days.

In an embodiment, the feed efficiency of a ruminant is improved by about 1 to 5%.

In an embodiment, the feed efficiency for lean tissue deposition of a ruminant is up to about 50% improvement above feeding ractopamine alone over the same period.

In a third aspect, there is provided use of caffeine in an animal feed containing ractopamine to extend benefit of ractopamine in a ruminant.

The present technology is particularly suitable for feed lots for cattle to improve body composition by increasing lean tissue and reducing adipose tissue deposition.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

In order that the present invention may be more clearly understood, preferred embodiments will be described with reference to the following examples.

MODE(S) FOR CARRYING OUT THE INVENTION

Materials and Methods
Ractopamine

Ractopamine (RAC) is a beta adrenergic agonist (β-agonist) that is approved for use as an in feed ingredient for livestock such as pigs, sheep and cattle. RAC has been widely demonstrated to improve feed efficiency, growth rates and carcass composition in these species, with the maximal response typically observed within the first three weeks of supplementation.

Ractopamine is a repartitioning agent belonging to the phenethanolamine class of compounds. Phenethanolamines bind directly to either α- and/or β-adrenergic receptors situated on cell membranes, stimulating the release of chemical signals involved in mammalian growth and development. Adrenaline and noradrenaline are natural compounds in this class that bind to both the α- and β-adrenergic receptors. Ractopamine is a synthetic phenethanolamine that binds to β-adrenergic receptors resulting in physiological responses that increase lean tissue deposition in livestock.

In contrast, Ephedrine is not a β-agonist (i.e it does not bind to β-adrenergic receptors). Ephedrine is an indirect-acting synthetic non-catecholamine, stimulating the release of noradrenaline which may then act on β-adrenergic receptors. There are many drugs in the phenethanolamine class of compounds with vastly different specificity for particular cell types and with markedly different effects upon fat and other metabolism in animals. A universal effect of β-agonists is an acute increase in plasma non-esterified fatty acids (NEFA) as a result of β-adrenergic stimulation of fat mobilization whereas ephedrine has no acute effect on plasma NEFA.

There have been many exogenous compounds produced for use in human medicine, particularly for the treatment of asthma (relaxation and dilation of the airways) or to improve cardiovascular function. Along with their differing specificity, there are also marked differences in the clearance rate of compounds in this class, with ractopamine cleared very rapidly compared to many of the compounds developed for medicinal purposes. Given the differences in activity and specificity within this class of compound, ractopamine would not be expected (and if fact does not) to act similarly to a compound such as ephedrine that is not a phenethanolamine and does not act directly on β-adrenergic receptors.

Ractopamine (RAC) is sold by Elanco Animal Health (Greenfield, Ind. USA) under the brand Optaflexx™ as a free-flowing granular material, manufactured to provide 100 grams of ractopamine hydrochloride (active ingredient) per kilogram of product for ruminants such as cattle. Optaflexx™ is packaged in 11.34 kg laminated bags with moisture barrier within the plies. Optaflexx™ is manufactured to meet three-year expiry dating.

The manufacture offers the following information on its Optaflexx™ product.

Optaflexx™ is marketed for use in finishing beef cattle to increase live weight gain, improve feed efficiency, increase hot carcass weight and increase red meat yield when fed for the last 28 to 42 days of the finisher period.

When feed as a complete feed, Optaflexx™ is marketed for increased rate of weight gain, improved feed efficiency and increased carcass leanness in cattle fed in confinement for slaughter during the last 28 to 42 days on feed and fed at a rate of 11 to 27 mg/kg complete feed or 90 to 430 mg ractopamine per head per day. To ensure adequate mixing, an intermediate blending step should be performed prior to manufacturing a complete feed.

Fed as a top dress, Optaflexx™ is marketed to increase rate of weight gain and improve feed efficiency in cattle fed in confinement for slaughter during the last 28 to 42 days on feed and fed at a rate of 70-400 mg ractopamine per head per day.

Directions are to feed continuously as the sole ration to finishing livestock intended for slaughter for no longer than 6 weeks. Dietary specifications should be determined in consultation with a recognized nutritional advisor in order to optimize Optaflexx™ effects on performance, carcass parameters and beef quality.

Caffeine

Caffeine was obtained from CSPC Innovation Pharmaceutical Co Ltd—a Chinese off-patent manufacturer. Caffeine is readily available in bulk from fine chemical suppliers. Caffeine can be added to the complete animal feed at a concentration of from about 0.02 g/kg to 5 g/kg (w/w) caffeine. The animal feed after supplementation can have from about 0.1 g/kg to 1 g/kg (w/w) caffeine. A final concentration of about 0.5 kg/t caffeine was used in the bulk feed.

Animal Feed Supplement

An animal feed supplement containing ractopamine and caffeine can be prepared by adding caffeine to a bulk pack of Optaflexx™ to provide the desired concentrated amounts of ractopamine and caffeine. The feed supplement can then be added to bulk animal feed to provide the desired amounts of ractopamine and caffeine to be consumed by the animal.

In one embodiment, the animal feed supplement contains from about 1 to 50 g/kg ractopamine hydrochloride and from about 50 to 950 g/kg caffeine for mixing with bulk complete animal feed to provide a desired final concentration of ractopamine and caffeine to the animal feed.

Ractopamine and caffeine can be mixed in any suitable carrier material, such as milled grain or other edible material and pelleted by standard techniques to give a concentrated supplement for adding to animal feed to give a final desired feeding quantity of ractopamine and caffeine.

The combined product containing ractopamine and caffeine can also be used to prepare a top dress feed for ruminants such as cattle and sheep.

Animals and Treatments

Lambs were used in this study as the model animal representing ruminants. Previous research has shown similar growth performance, feed efficiency and carcass benefits from the inclusion of Ractopamine in cattle and lamb diets. Given this, it is expected that the outcomes from feeding RAC and caffeine in combination to finishing lambs can be translated to expected results in other ruminants such as cattle. The surprising results found in lambs show promise for use of RAC and caffeine in other ruminants, particularly cattle where RAC is an approved animal feed additive.

A total of 36 male lambs (Border Leister×Merino) were selected at approximately 14 weeks of age and housed in pens of two lambs per pen in a naturally ventilated shed. Lambs were fed a commercial lamb finisher diet for a 14 day acclimatisation period prior to the start of the test period. In addition, all lambs were offered 250 g lucerne hay per day as roughage. At the start of the test period, lambs were individually weighed (average weight 29.8 kg±0.29 kg), ear tagged and the pen randomly allocated to one of three dietary treatments:

A: Control (no RAC or Caffeine for the entire 56 day test period)

B: RAC (20 ppm (20 g/t) RAC for the entire 56 day test period)

C: RAC+Caffeine (20 ppm (20 g/t)) RAC offered from day 0 to day 21, followed by 20 ppm (20 g/t) RAC plus 0.5 kg/t caffeine offered from day 21 to day 56).

The dietary compositions of the three experimental diets are displayed in Table 1. Diets were pelleted and fed ad libitum for the entire test period, while water was also freely available at all times. In addition to the pelleted test feeds, each lamb was offered 200 g lucerne hay per day (floor fed) as an additional source of roughage.

TABLE 1

Ingredient composition and analysed nutrient profile of each of the experimental finisher diets, % of diet (as fed basis).

|  | Control | RAC | RAC + Caffeine |
|---|---|---|---|
| Wheat | 25.0 | 25.0 | 25.0 |
| Barley | 25.0 | 25.0 | 25.0 |
| Millmix | 27.5 | 27.5 | 27.5 |
| Canola meal | 12.0 | 12.0 | 12.0 |
| Soyabean meal | 3.0 | 3.0 | 3.0 |
| Water | 1.0 | 1.0 | 1.0 |
| Molasses | 1.5 | 1.5 | 1.5 |
| Limestone | 1.5 | 1.5 | 1.5 |
| Dicalcium phosphate | 1.0 | 1.0 | 1.0 |
| Calcium sulphate | 0.35 | 0.35 | 0.35 |
| Ammonium chloride | 0.40 | 0.40 | 0.40 |
| Urea | 0.50 | 0.50 | 0.50 |
| Vitamin and mineral premix | 0.05 | 0.05 | 0.05 |
| Bovatec | 0.017 | 0.017 | 0.017 |
| Salt | 1.2 | 1.2 | 1.2 |
| RAC |  | 0.10 | 0.10 |
| Caffeine |  |  | 0.05 |
| Estimated nutrient composition, %* | | | |
| Dry matter | | | |
| Crude protein | 17.05 | 17.04 | 17.04 |
| Fat | 1.80 | 1.80 | 1.80 |
| ME | 11.00 | 11.00 | 11.00 |
| NDF | 22.10 | 22.10 | 22.10 |
| ADF | 8.98 | 8.98 | 8.98 |
| Calcium | 1.00 | 1.00 | 1.00 |
| Total phosphorus | 0.77 | 0.77 | 0.77 |

Management and Measures

Lambs were shorn prior to entry to the facility to minimise the impact of wool growth on rate of gain measurements and body composition analysis. Individual weights were recorded periodically throughout the test period (Days 0, 21, 35 and 56), while intake of the pelleted test diets was measured by feed disappearance and feed efficiency subsequently calculated.

No attempt was made to measure feed residues of the lucerne hay as the lambs consumed this rapidly and the volume of wastage was considered insignificant.

Dual energy x-ray absorptiometry (DXA) scanning was undertaken using a Hologic X-Ray Bone Densitometer (Hologic Inc, Waltham, Mass., USA) at day 21 and day 56 of the test period. All lambs were weighed on the day of scanning (prior to anaesthesia). Lambs were sedated using xylazine (administered intramuscularly) and anaesthetised with ketamine intra venously under veterinary direction. Once anaesthetised, lambs were positioned in a ventral recumbency with their hind legs extended and forelegs positioned caudally to accommodate the DXA regional analysis software. The whole body scan mode was used for each animal, with the length of the scan adjusted for the length of the lamb. Following DXA analysis, lambs were monitored by a veterinarian for full recovery from anaesthesia. As the DXA software generates body composition estimates for humans, the raw DXA output from each scan was adjusted for lambs using equations developed by comparisons with actual empty body chemical composition (Hunter 2000).

Statistical Analyses

Data were subjected to an analysis of variance (ANOVA) for the main effect of dietary treatment. Data for treatments B and C were pooled for the initial 21 day feeding period as both treatment groups were fed the same diet during this time period. The experimental unit for all analyses was the pen of ruminant. All analyses were performed using Genstat 16$^{th}$ Edition (Payne R W, Harding S A, Genstat Committee 2005 Genstat release 8 reference manual, USN International: Oxford UK).

Results

The impact of RAC inclusion during the initial 21 day feeding period is displayed in Table 2. Lambs offered the RAC diet tended to gain weight more quickly than the animals offered the control diet (P=0.097). While feed intake increased slightly with RAC inclusion (not significant), the efficiency of feed utilisation for weight gain tended to be superior in the RAC fed lambs (P=0.101). Live weight at day 21 tended to be greater in the lambs offered the RAC diet (P=0.109).

TABLE 2

Impact of dietary RAC on growth performance and feed efficiency from day 0 to day 21.

|  | Control | RAC | sed | P-value |
|---|---|---|---|---|
| Live weight day 0 | 29.8 | 29.8 | 0.63 | 0.92 |
| Live weight day 21* | 36.2 | 37.9 | 1.01 | 0.109 |
| ADFI (kg/d) | 1.32 | 1.40 | 0.058 | 0.17 |
| ADG (kg/d) | 0.306 | 0.388 | 0.047 | 0.097 |
| FCE (gain/feed) | 0.23 | 0.28 | 0.029 | 0.101 |

*Day 0 weight included as a covariate in the analysis

Growth performance and feed efficiency for the subsequent period from day 21 are displayed in Table 3. The addition of caffeine to the RAC diet significantly reduced feed intake from day 21 to 35 (P=0.022), with a strong trend for reduced intake when considered from day 21 to 56 (P=0.056). Growth performance tended to be reduced initially (day 21 to 35) with the introduction of caffeine to the RAC diet (P=0.098), however this was not significant over the extended period from day 21 to 56 (P=0.69).

Feed efficiency (gain to feed) was not significantly influenced by dietary treatment from day 21 to 56, however there are some interesting trends to note. Between day 21 and day 35, feed efficiency continued to be superior when lambs were offered the RAC diet. During the subsequent period from day 35 to 56, the feed efficiency of the RAC treatment group declined while the RAC+caffeine treatment group improved due to faster growth rates and slightly reduced feed consumption. Over the entire test period feed intake was numerically reduced in the RAC+caffeine treatment group, while growth rates were fastest in the RAC fed lambs and slowest in the control group. Feed efficiency was not significant over the entire test period, but was numerically superior in both RAC treatment groups compared to the controls.

TABLE 3

Impact of dietary RAC with or without caffeine on growth performance and feed efficiency of lambs

|  | Control | RAC | RAC + Caffeine | sed | P-value |
|---|---|---|---|---|---|
| Live weight (kg)* | | | | | |
| Day 0 | 29.8 | 29.6 | 30.1 | 0.74 | 0.79 |
| Day 21 | 36.2 | 38.2 | 37.7 | 1.21 | 0.26 |
| Day 35 | 40.4 | 43.6 | 40.7 | 1.43 | 0.079 |
| Day 56 | 44.4 | 47.3 | 45.4 | 1.76 | 0.28 |
| Day 21-35 | | | | | |
| ADFI | 1.69 | 1.77 | 1.52 | 0.078 | 0.022 |
| ADG | 0.295 | 0.380 | 0.283 | 0.045 | 0.098 |
| FCE | 0.176 | 0.214 | 0.186 | 0.0268 | 0.37 |

TABLE 3-continued

Impact of dietary RAC with or without caffeine on growth performance and feed efficiency of lambs

|  | Control | RAC | RAC + Caffeine | sed | P-value |
|---|---|---|---|---|---|
| Day 35-56 | | | | | |
| ADFI | 1.73 | 1.77 | 1.63 | 0.103 | 0.38 |
| ADG | 0.190 | 0.177 | 0.221 | 0.058 | 0.74 |
| FCE | 0.130 | 0.113 | 0.136 | 0.0291 | 0.72 |
| Day 21-56 | | | | | |
| ADFI | 1.76 | 1.82 | 1.61 | 0.081 | 0.056 |
| ADG | 0.239 | 0.266 | 0.229 | 0.043 | 0.69 |
| FCE | 0.137 | 0.144 | 0.142 | 0.0247 | 0.96 |
| Day 0-56 | | | | | |
| ADFI | 1.59 | 1.67 | 1.53 | 0.065 | 0.12 |
| ADG | 0.265 | 0.317 | 0.285 | 0.031 | 0.26 |
| FCE | 0.166 | 0.189 | 0.187 | 0.0159 | 0.30 |

*Weight at day 0 included as a covariate in the analysis of subsequent live weight data.

TABLE 4

Influence of dietary treatments on body composition between day 21 and day 56

|  | Control | RAC | RAC + Caffeine | sed | P-value |
|---|---|---|---|---|---|
| Day 21^ | | | | | |
| Adipose tissue (%) | 20.70 | 19.18 | 19.30 | 0.365 | 0.002 |
| Lean tissue (%) | 75.68 | 76.84 | 76.83 | 0.297 | 0.003 |
| Bone mineral content (%) | 2.92 | 2.95 | 2.88 | 0.077 | 0.65 |
| Day 56* | | | | | |
| Adipose tissue (%) | 23.51 | 22.90 | 21.95 | 0.958 | 0.28 |
| Lean tissue (%) | 72.23 | 72.64 | 73.41 | 0.80 | 0.34 |
| Bone mineral content (%) | 2.86 | 3.01 | 2.83 | 0.059 | 0.015 |
| Feed efficiency for lean tissue deposition (kg lean tissue gain: kg feed intake) | | | | | |
| Day 21-56 | 0.082 | 0.073 | 0.111 | 0.019 | 0.15 |

^Live weight day 21 included as a covariate
*Live weight day 56 included as a covariate in the analysis The DXA body composition data supports the trends in feed efficiency during the latter growth period. At day 21, analysis of the pooled data indicates lambs previously offered the RAC diet had a greater percentage of lean tissue compared to the control group (75.68 and 76.83% for the control and RAC treatment groups respectively, P<0.001, sed 0.257) and reduced adipose tissue (20.70 and 19.24% respectively, P<0.001, sed 0.317). When analysed over the three treatments, the percentage of lean and adipose tissue in the lambs was similar between the RAC and RAC+caffeine treatment groups at day 21 (Table 4). Body composition data at day 56 suggests a trend for a reduced percentage of adipose tissue in the body and increased lean tissue percentage when lambs had been offered the RAC+caffeine diet during the preceding 35 days. Interestingly bone mineral content was increased in the lambs offered RAC alone. Feed efficiency for lean tissue deposition (lean tissue gain: kg feed intake) was numerically superior in the RAC+caffeine treatment group (Table 4).

Implications

Lambs were used in this study as a model for testing this method in ruminant species given the similar response to ractopamine alone in both cattle and sheep.

The results from this investigation suggest that there may be synergistic effects from the use of RAC in combination with caffeine for lambs (ruminant) and other ruminant species (cattle). This study was designed to test the benefits of including caffeine into a RAC lamb diet after the RAC diet had been fed for an initial three week period. The results from this investigation support the hypothesis that RAC and caffeine in combination can be used to extend the response of RAC beyond the standard 2-3 week period, improving feed efficiency for lean tissue deposition during the latter growth periods and directing more nutrients to lean tissue deposition rather than fat deposition.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of increasing ractopamine response in a ruminant, the method comprising feeding a ruminant an animal feed containing a synergistic combination of ractopamine and caffeine to extend the response to ractopamine in the ruminant;
wherein the response to ractopamine in the ruminant is extended for at least 7 days.

2. The method according to claim 1, wherein the ruminant is selected from the group consisting of cattle, sheep, goat, and deer.

3. The method according to claim 1, wherein the ruminant is cattle.

4. The method according to claim 1, wherein the ractopamine response is improved feed efficiency for lean tissue deposition in the ruminant.

5. The method according to claim 1, wherein the ractopamine response is extended in the ruminant past 21 days.

6. The method according to claim 1; wherein the response to ractopamine in the ruminant is extended for at least 14 days.

7. The method according to claim 1, wherein the ruminant is fed the animal feed over a period of up to 60 days.

8. The method according to claim 7, where the ruminant is fed the animal feed for a period of 21 to 35 days.

9. The method according to claim 1, wherein the ractopamine is ractopamine hydrochloride.

10. The method according to claim 1, wherein the animal feed contains from 1 mg/kg to 50 mg/kg (w/w) ractopamine and from 0.02 g/kg to 5 g/kg (w/w) caffeine.

11. The method according to claim 10, wherein the animal feed contains from 5 mg/kg to 20 mg/kg (w/w) ractopamine and from 0.1 g/kg to 1 g/kg (w/w) caffeine.

12. The method according to claim 11, wherein the animal feed contains 20 mg/kg ractopamine and 0.5 g/kg caffeine.

13. The method according to claim 1, wherein the animal feed is a typical ruminant finishing feed containing essential dietary requirements for a ruminant or as a top dress diet formulation.

14. The method according to claim 13, wherein the animal feed contains a range of energy and protein sources selected from wheat, barley, millmix, sorghum, corn, soybean meal, lupins, canola meal, molasses, and urea.

15. The method according to claim 1, wherein the ruminant is fed an animal feed containing ractopamine for a first feeding period prior to feeding the ruminant the animal feed containing a synergistic combination of ractopamine and caffeine.

16. The method according to claim 15, wherein the first feeding period is from 7 to 21 days.

17. The method according to claim 15, wherein during the first feeding period the animal feed contains from 1 mg/kg to 50 mg/kg (w/w) ractopamine.

18. The method according to claim 15, wherein the ruminant is fed ractopamine up to 60 days.

19. The method according to claim 1, wherein the feed efficiency of the ruminant is improved by up to 50%.

20. The method according to claim 1, wherein the feed efficiency of the ruminant is up to 50% improvement above feeding ractopamine alone over the same period.

21. The method according to claim 1, wherein the feed efficiency for lean tissue deposition of a ruminant is improved by 1 to 50%.

* * * * *